United States Patent
Poole et al.

(10) Patent No.: US 7,799,229 B2
(45) Date of Patent: Sep. 21, 2010

(54) PROCESS FOR THE REMOVAL OF CATALYTIC METALS AND PROMOTER METALS FROM CARBONYLATION PROCESS STREAMS

(75) Inventors: Andrew David Poole, East Riding of Yorkshire (GB); Stephen James Smith, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 697 days.

(21) Appl. No.: 11/596,590

(22) PCT Filed: Apr. 22, 2005

(86) PCT No.: PCT/GB2005/001529

§ 371 (c)(1),
(2), (4) Date: Aug. 24, 2007

(87) PCT Pub. No.: WO2005/113479

PCT Pub. Date: Dec. 1, 2005

(65) Prior Publication Data

US 2008/0230481 A1  Sep. 25, 2008

(30) Foreign Application Priority Data

May 19, 2004 (GB) ................................. 0411185.2

(51) Int. Cl.
*C02F 1/42* (2006.01)

(52) U.S. Cl. ..................................................... 210/688

(58) Field of Classification Search ................... 210/688
See application file for complete search history.

(56) References Cited

U.S. PATENT DOCUMENTS 3,716,626 A    2/1973  Himmele et al.
5,466,876 A *  11/1995  McClarron et al. .......... 562/608
6,329,435 B1 * 12/2001  Klipper et al. ................ 521/33

FOREIGN PATENT DOCUMENTS

EP  0 482 787 A2    4/1992
EP  0 618 185 A1   10/1994
EP    618185 A1 * 10/1994
SU  1 160 684 A1    1/1996

OTHER PUBLICATIONS

Letter dated Feb. 26, 2009 with English Translation of Russian Office Action dated Jan. 16, 2009; Russian Patent Application No. 2006 144 807 (3 pgs).

* cited by examiner

*Primary Examiner*—Chester T Barry
(74) *Attorney, Agent, or Firm*—Nixon & Vanderhye

(57) ABSTRACT

Process for the selective removal of Iridium carbonylation catalyst metal and/or at least one promoter selected from ruthenium, osmium and rhenium from a liquid composition comprising a carbonylation product, iridium carbonylation catalyst metal and/or the promoter metal, corrosion metals and optionally alkali or alkaline earth metals. The process is carried out by contacting the liquid composition with a chelating resin to remove at least a portion of the iridium carbonylation catalyst metal and/or at least one promoter metal contained in the liquid composition. The chelating resin contains at least one thiourea functional group. The process is suitable for treating process streams obtained in the production of carboxylic acids and/or carboxylic anhydrides.

26 Claims, No Drawings

PROCESS FOR THE REMOVAL OF CATALYTIC METALS AND PROMOTER METALS FROM CARBONYLATION PROCESS STREAMS

This application is the U.S. National Phase of International Application PCT/GB2005/001529, filed 22 Apr. 2005, which designated the U.S. PCT/GB2005/001529 claims priority to British Application No. 0411185.2 filed 19 May 2004. The entire content of these applications are incorporated herein by reference.

The present invention relates to the recovery of Group VIII carbonylation catalyst and/or promoter metals from process streams obtained in carbonylation processes.

The production of carboxylic acids and derivatives thereof such as esters and anhydrides by the carbonylation of alcohols or reactive derivatives thereof in the presence of a Group VIII metal catalyst such as rhodium or iridium or mixtures thereof and a catalyst promoter is well known and is described, for example, in EP-A-0144935, EP-A-0643034 and U.S. Pat. No. 6,211,405. Typically, where the catalyst is iridium the catalyst promoter may be selected from metals such as ruthenium, osmium, rhenium, tungsten, zinc, cadmium, indium, gallium and mercury as described, for example, in EP-A-0849248 and EP-A0643034. Where the catalyst is rhodium the catalyst promoter is typically lithium.

Typically, in the operation of a carbonylation process, such as the production of acetic acid, the liquid reaction composition from the reactor is passed to one or more flash separation vessels wherein the catalyst components are separated from the more volatile components. The liquid fraction containing the catalyst components is recycled to the reactor and the vapour fraction comprising acetic acid, methyl acetate and methyl iodide is passed to the purification section of the process. However, it has been found that a low level of catalyst and/or promoter metals may become entrained or contained in the vapour fraction and the metals are thus passed to the product purification section of the process from where they may be removed from the acetic acid product as a waste stream and ultimately disposed of.

The catalyst and promoter metals are often expensive and significant cost advantages may be achieved by minimizing the loss of such metals from the process.

Methods of removing metallic components from a carbonylation reaction product stream are known in the art. U.S. Pat. No. 6,627,770 describes the use of a resin comprising heterocyclic nitrogen-containing repeat units to sequester Group VIII metals from the product stream of a liquid phase, homogeneously-catalysed carbonylation reaction. In such a process, the vapour fraction emanating from the flash vessel is contacted with the aforementioned resin, which removes entrained or volatile Group VIII metals contained therein.

U.S. Pat. No. 6,329,435 describes the preparation of monodisperse, crosslinked bead polymers containing thiourea groups and their use for absorbing metal compound, in particular heavy metal compounds or noble metal compounds.

EP-A-1203777 describes a thiourea-functionalised resin for enhanced uptake of iron and rhodium from hydrogenated nitrile rubber.

EP-A-618185 discloses a process for the removal of corrosion metal contaminants from a liquid composition comprising a carboxylic acid or carboxylic acid anhydride using a chelating resin.

Thus there remains a need for a process for the recovery of catalyst and/or promoter metals from carbonylation process streams. In particular, it would be advantageous if the catalyst and/or promoter metals could be recovered in preference to other metals typically contained in carbonylation process streams such as corrosion metals and alkali metals added to aid product purification. Typically, the corrosion metals found in carbonylation process streams include iron, nickel, chromium and molybdenum.

It has now been found that chelating resins having thiourea functional groups can be used to selectively remove Group VIII carbonylation catalyst metals and/or promoter metals from carbonylation process streams and, in particular to remove the catalyst metals in preference to corrosion metals contained in a carbonylation process stream.

Accordingly, the present invention provides a process for the selective removal of Group VIII carbonylation catalyst metals and/or promoter metals from a liquid composition comprising a carbonylation product, at least one Group VIII carbonylation catalyst metal and/or promoter metal, corrosion metals and optionally alkali or alkaline earth metals which process comprises contacting said liquid composition with a chelating resin to remove at least a portion of the Group VIII carbonylation catalyst metal and/or promoter metal contained in the liquid composition and wherein the chelating resin comprises at least one thiourea functional group.

Chelating resins have functional groups which attach to the metal to be removed. The chelating resins suitable for use in the process of the present invention have at least one thiourea functional group. The following chelating resin may be used in the process of the present invention:

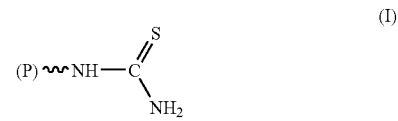

(I)

wherein P represents a chemical backbone.

The chemical backbone may be organic or inorganic. Suitably, the organic backbone may be a polymer backbone, for example polystyrene, polyacrylate, polymethacrylate, polyethylene or polypropylene, preferably polystyrene. The polymer backbone, such as polystyrene, may optionally be crosslinked, for example, with divinylbenzene, divinyl toluene and trivinylbenzene, especially divinylbenzene.

The chelating resin may be macroporous, or may be of the gel-type. Macroreticular resins which comprise porous and interconnected gel phases resulting in a macroporous structure may also be employed.

An example of a chelating thiourea-functionalised resin having a polymeric backbone suitable for use in the process of the present invention would be Lewatit TP214 (trademark) available from Sybron Chemicals.

Chelating resins having an inorganic backbone may also be used. Examples of suitable inorganic backbones include silica, alumina, titania, ceria, zirconia clays and zeolites such as aluminosilicates and aluminophosphates.

Chelating resins having backbones with inorganic and organic moieties may also be employed in the process of the present invention.

Preferred chelating resins for use in the process of the present invention have a polymeric backbone.

Treatment of the liquid composition is usually effected by passing the liquid composition through a fixed bed of the resin. The treatment of the liquid composition may be carried out as a batch, semi-continuous or continuous operation employing methods and techniques well known in the art of chelating resins. Continuous operation is preferred.

The liquid composition may be contacted with the chelating resin at any suitable temperature above the freezing point of the liquid composition and below the temperature at which the resin and/or liquid composition exhibits unacceptable decomposition. Suitably, the process may be carried out at a temperature in the range 0 to 100° C., preferably in the range 5 to 80° C. Pressure is not a critical variable and generally, atmospheric or pressures slightly above atmospheric pressure may be employed. However, superatmospheric or subatmospheric pressures may be used if desired.

The rate of flow (liquid hourly space velocity) of the liquid composition through a fixed bed of the chelating resin will, in general, be in the range 1 to 20 $h^{-1}$, such as in the range 1 to 12 $h^{-1}$.

The liquid composition to be treated by the process of the present invention may be treated in-situ or may be treated off-line.

Contact of the liquid composition is ceased at or before the chelating resin has reached its capacity for the catalyst and promoter metals. The chelating resin may then be treated by any suitable means to recover the metals. Regeneration of the chelating resin may be achieved by the methods recommended by the manufacturers.

More than one chelating resin bed may be used such that whilst the liquid composition is being passed through one resin bed one or more other resin beds are being regenerated.

Alternatively, the chelating resin may be subjected to a destructive process in order to recover the metals. Such destructive methods include combustion, pyrolysis or chemical decomposition of the resin. The resultant residue may be treated or digested with a suitable dissolving medium, such as a Bronsted acid, such that the catalyst and promoter metals are solubilised for recovery.

The process of the present invention is particularly applicable to the removal of Group VIII carbonylation catalysts such as iridium, rhodium and mixtures thereof and their associated promoter metals such as ruthenium, osmium, rhenium and mercury from liquid compositions comprising corrosion metals typically found in carbonylation processes such as iron, nickel, chromium, manganese, zinc and molybdenum, particularly iron and nickel.

The process of the present invention is particularly applicable to the removal of Group VIII metals and/or promoter metals from carbonylation process streams obtained from the carbonylation of an alcohol, such as methanol and/or a reactive derivative thereof in the presence of a Group VIII carbonylation catalyst, an alkyl halide co-catalyst, a catalyst promoter and optionally a finite concentration of water.

The liquid composition treated in the process of the present invention may also comprise alkali or alkaline earth metals such as lithium, sodium and/or potassium. Salts of the alkali/alkaline earth metals are typically employed as catalyst co-promoters/stabilisers in rhodium catalysed carbonylation processes and/or are added to distillation columns as purification aids.

The liquid composition to be treated in the process of the present invention may also comprise unconverted carbonylation reactant, for example, alcohols, ethers, halides and/or esters. Suitably, the carbonylation reactant may comprise $C_1$ to $C_{10}$ alcohols, such as methanol; dialkyl ethers wherein the alkyl groups independently have 1 to 10 carbon atoms, for example, dimethylether; alkyl halides having 1 to 10 carbon atoms, for example, methyl iodide and esters of $C_1$ to $C_{10}$ alcohols with $C_2$ to $C_{11}$ carboxylic acids, for example, methyl acetate. The liquid composition may also comprise an iodide of a quaternary amine, phosphine, arsenic or antimony compound or an iodide salt of an alkali or alkaline earth metal.

Suitable quaternary phosphine iodide salts are described in U.S. Pat. No. 4,333,884. Suitable quaternary amine iodide salts are described in U.S. Pat. No. 4,333,884, U.S. Pat. No. 4,430,273 and EP-A-0479463. The liquid composition treated in the process of the present invention may also comprise a solvent compatible with the carbonylation process from which the liquid composition is derived. Where the liquid composition is derived from a carbonylation process for the production of a carboxylic acid, the liquid composition may also comprise water.

Suitably, the liquid composition is derived from the liquid reaction composition of a liquid phase carbonylation reaction for the production of carboxylic acids and/or carboxylic anhydrides, preferably acetic acid and/or acetic anhydride by the carbonylation of alcohols, ethers, esters and/or halides in the presence of a rhodium or iridium carbonylation catalyst, a halogen-containing carbonylation co-catalyst and a carbonylation catalyst promoter/stabiliser.

Suitable rhodium catalysed carbonylation processes are described, for example, in GB 2146637, U.S. Pat. No. 4,994,608, U.S. Pat. No. 5,001,259, U.S. Pat. No. 5,026,908, EP-A-0144936 and EP-A-0144935 which relate to the production of carboxylic acids by carbonylation; U.S. Pat. No. 5,003,104 which describes carbonylation processes for the production of carboxylic acids and carboxylic anhydrides; U.S. Pat. No. 4,374,070 which describe the preparation of acetic anhydride by carbonylation, EP-A-0087870 which describes the production of acetic anhydride with or without the net production of acetic acid.

Suitable iridium catalysed carbonylation processes for the production of carboxylic acid anhydrides are described in GB 2,333,773.

Suitable rhodium carbonylation catalysts are described, for example, in EP-A-0 161 874, U.S. Pat. No. 6,211,405 and EP-A-0728727. Suitable iridium carbonylation catalysts are described, for example, in GB 2,333,773.

Preferably, the rhodium catalyst concentration in the liquid reaction composition is in the range 100 to 2500 ppm by weight of rhodium.

The liquid composition may also be suitably derived from the liquid reaction composition of a liquid phase carbonylation reaction for the production of carboxylic acids preferably acetic acid by carbonylation of alcohols, ethers, esters and/or halides in the presence of an iridium carbonylation catalyst or a mixture of rhodium and iridium carbonylation catalysts, an alkyl halide co-catalyst, a catalyst promoter and a finite concentration of water.

Suitable iridium catalysed carbonylation processes for the production of carboxylic acids such as acetic acid are described, for example, in EP-A-0643034, EP-A-0752406, EP-A-0846674, EP-A-0849249, EP-A-0849251 and EP-A-0849248.

Suitable iridium carbonylation catalysts are described, for example in EP-A-0 643 034 and EP 0 752 406.

Preferably, the iridium catalyst concentration in the liquid reaction composition is in the range 100 to 6000 ppm by weight of iridium.

Suitable iridium carbonylation catalyst promoters are, for example, ruthenium, osmium, rhenium and mercury, preferably ruthenium and osmium.

A suitable iridium promoter concentration is 400 to 5000 ppm.

The liquid carbonylation reaction composition may also comprise an alkyl halide co-catalyst such as methyl iodide. Preferably, the concentration of the alkyl halide co-catalyst, such as methyl iodide, in the liquid carbonylation reaction composition is in the range 1 to 20% by weight, preferably 2 to 16% by weight.

Water may be formed in situ in the liquid reaction composition or may be introduced into the carbonylation reactor together with or separately from the other components of the reaction composition. Preferably, the concentration of water in the liquid reaction composition is in the range 0.1 to 15% by weight, more preferably, 1 to 15 wt %, especially 1 to 10 wt %.

Where a carboxylic anhydride is the carbonylation product, the liquid reaction composition is substantially anhydrous. By substantially anhydrous is meant less than 0.1 wt % water.

The carbonylation product may be a carboxylic acid having from 1 to 10 carbon atoms or carboxylic anhydride thereof and is preferably acetic acid and/or acetic anhydride.

Typically, carbonylation processes operate at 100-300° C. and at elevated pressure (15 to 200 barg) with a partial pressure of carbon monoxide of 2-30 atmospheres and may be carried out in one or more reaction zones.

In a typical liquid-phase carbonylation process to which the process of the present invention is applicable, liquid reaction composition is withdrawn from the one or more carbonylation reactors and passed to a flash zone at a pressure below that of the reactor(s) wherein with or without the addition of heat, a liquid fraction comprising the majority of the carbonylation catalyst and, if employed, the majority of the promoter, is separated from a vapour fraction comprising entrained or contained carbonylation catalyst and/or catalyst promoter species, carbonylation product, carbonylatable reactant, water and alkyl halide co-catalyst and non-condensable gases such as nitrogen, carbon monoxide, hydrogen and carbon dioxide; at least a portion of the liquid fraction is recycled to the carbonylation reactor(s) and the vapour fraction is passed to the product purification section which generally comprises one or more distillation zones. In a first distillation column (generally referred to as the light ends column) carbonylation product is separated from the light components (alkyl halide co-catalyst and unconverted reactant). The light components are removed overhead, and recycled to carbonylation reactor(s). A crude carbonylation product stream is removed from the first distillation column and fed to one or more further distillation columns to obtain a carbonylation product of commercially acceptable quality. Where the carbonylation product is a carboxylic acid, the crude carboxylic acid from the light ends column may be fed to a drying column to obtain a dry crude acid product which is then fed to a heavy ends distillation column to remove high boiling impurities such as propionic acid as bottoms from the column and to recover the carboxylic acid product. In some carboxylic acid processes, light ends removal and drying may be carried out in a single combined column.

The amount of catalyst and/or promoter metal entering the product purification section will depend on various factors such as the carbonylation reaction conditions and also on the configuration of the carbonylation process equipment.

The liquid composition to be treated according to the process of the present invention may be derived from any process stream comprising carbonylation catalyst and/or promoter. Suitably, a liquid composition to be treated according to the process of the present invention may be obtained from a distillation column stream such as from the base of a heavy ends column and/or from the base of a combined light ends and drying column and/or from a drying column.

The process of the present invention may also be used to treat liquid compositions containing Group VIII carbonylation catalyst metals and/or promoter metals derived from gas phase (heterogeneous) carbonylation processes.

The present invention will now be illustrated by way of example only and with reference to the following Examples.

EXAMPLE 1

The chelating resins used were Lewatit TP207, TP260 and TP214 (Sybron Chemicals Inc.) The resins are cross-linked macroreticular polystyrene resins, and contain different chelating functional groups, namely iminoacetate (TP207), aminophosphate (TP260) and thiourea (TP214). Prior to use the resins were pre-swollen in acetic acid. In addition, a mineral acid pre-treatment was performed on TP207 prior to treatment with acetic acid in order to remove sodium ions.

The liquid composition to be treated was derived from a carbonylation process for the production of acetic acid and comprised acetic acid, methyl acetate, methyl iodide, water, approximately 2000 ppm Ir, 4300 ppm Ru, 90 ppm Li, and varying levels of corrosion metals within the following ranges: Fe, 14-60 ppm; Ni, 14-92 ppm; Cr, 8-20 ppm; Mo, 18-60 ppm; Zn, 4-6 ppm.

The liquid composition was passed through 30 mL of a fixed bed of resin at a temperature of 20° C., a pressure of 1.5 barg, and at a liquid hourly space velocity (LHSV) of 10. The resin was removed from the vessel, washed with water and dried in an oven at 80° C. for 16 hours. The metal content retained by the resin was then determined by X-ray fluorescence for iridium and ruthenium, atomic absorption spectroscopy for lithium, and inductively couple plasma-atomic emission spectroscopy for the corrosion metals. The results are shown in Table 1.

TABLE 1

| | | Metal Content of Resin | | | | | | | |
|---|---|---|---|---|---|---|---|---|---|
| Resin | Hours On Stream | Ir wt % | Ru wt % | Fe ppm | Ni ppm | Cr ppm | Mo ppm | Zn ppm | Li ppm |
| TP207 | 290 | 2.7 | 2.5 | 200 | 1200 | <50 | 300 | 550 | <25 |
| TP260 | 80 | 0.4 | 0.53 | 3600 | 950 | 100 | 1000 | 1400 | <25 |
| TP214 | 80 | 6.8 | 5.1 | 50 | 50 | <50 | <50 | 100 | <25 |

The results in Table 1 show that the chelating resin of the present invention (TP214) is superior to chelating resins which do not have thiourea functional groups for the selective removal of carbonylation catalyst and promoter metals.

EXAMPLE 2

The liquid composition to be treated in this Example was obtained from the base of a heavy ends distillation column of a carbonylation process to produce acetic acid. The metal content of the liquid composition is given in Table 2. 150 ml of the liquid composition and 15 ml of Lewatit TP214 (Sybron Chemicals Inc.) which had been soaked in glacial acetic acid was charged into a round-bottomed flask and stirred, using a magnetic follower, for a total of 48 hours at ambient temperature. 10 ml liquid aliquots were removed from the flask at periodic intervals and analysed for their metal content. The results are shown in Table 2.

TABLE 2

| | Metals Content | | | | | | | |
|---|---|---|---|---|---|---|---|---|
| Sample | Fe ppm | Cr ppm | Ni ppm | Mo ppm | Zn ppm | Ir ppm | Ru ppm | K wt % |
| Feed | 1600 | 450 | 420 | 100 | <5 | 5 | 240 | 2.19 |
| 1 hour | 1500 | 430 | 380 | 80 | <5 | <5 | 150 | 1.87 |

TABLE 2-continued

| | Metals Content | | | | | | | |
|---|---|---|---|---|---|---|---|---|
| Sample | Fe ppm | Cr ppm | Ni ppm | Mo ppm | Zn ppm | Ir ppm | Ru ppm | K wt % |
| 24 hours | 1500 | 430 | 350 | 80 | <5 | <5 | 90 | 1.85 |
| 48 hours | 1500 | 430 | 340 | 70 | <5 | <5 | 30 | 1.86 |

The results in Table 2 shows that the thiourea-functionalised chelating resin of the present invention retains the carbonylation catalyst metal and promoter metal in preference to the corrosion metals and the alkali metal.

The invention claimed is:

1. A process for the selective removal of Iridium carbonylation catalyst metal and/or at least one promoter selected from the group consisting of ruthenium, osmium and rhenium from a liquid composition comprising a carbonylation product, iridium carbonylation catalyst metal and/or said promoter metal, corrosion metals and optionally alkali or alkaline earth metals which process comprises contacting said liquid composition with a chelating resin to remove at least a portion of the iridium carbonylation catalyst metal and/or at least one promoter metal contained in the liquid composition and wherein the chelating resin comprises at least one thiourea functional group.

2. A process according to claim 1 wherein the liquid composition comprises alkali or alkaline earth metals.

3. A process according to claim 2 wherein the alkali metal is selected from the group consisting of lithium, sodium and potassium.

4. A process according to claim 1 wherein the chelating resin is of formula:

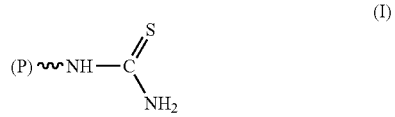

(I)

wherein P represents a chemical backbone.

5. A process according to claim 4 wherein the chemical backbone, P, is a polymer.

6. A process according to claim 5 wherein the polymer is selected from the group consisting of polystyrene, polyacrylate, polymethacrylate, polyethylene and polypropylene.

7. A process according to claim 5 or claim 6 wherein the polymer is a crosslinked polymer.

8. A process according to claim 7 wherein the crosslinked polymer is a crosslinked polystyrene.

9. A process according to claim 8 wherein the crosslinked polystyrene is a divinylbenzene polystyrene.

10. A process according to claim 4 wherein the chemical backbone, P, is selected from the group consisting of silica, alumina, titania, ceria, zirconia, clays and zeolites.

11. A process according to claim 4 wherein the chemical backbone, P, has inorganic and organic moieties.

12. A process according to claim 1 wherein the chelating resin is a macroporous resin or a gel resin.

13. A process according to claim 1 wherein the liquid reaction composition further comprises rhodium carbonylation catalyst metal.

14. A process according to claim 1 wherein the process is operated as a batch, semi-continuous or continuous process.

15. A process according to claim 1 wherein the liquid composition is contacted with the chelating resin at a temperature in the range 0 to 100° C.

16. A process according to claim 1 wherein the liquid hourly space velocity of the liquid composition is in the range 1 to 20 $h^{-1}$.

17. A process according to claim 1 wherein the liquid composition is treated in-situ or offline.

18. A process according to claim 1 wherein the liquid composition is a process stream obtained from a carbonylation process to produce a carbonylation product which is a carboxylic acid.

19. A process according to claim 18 wherein the carboxylic acid is acetic acid.

20. A process according to claim 1 wherein the liquid composition further comprises one or more components selected from the group consisting of unconverted carbonylatable reactant, a solvent, water and iodide ions.

21. A process according to claim 1 wherein the liquid composition is a process stream obtained from the carbonylation of an alcohol and/or reactive derivative thereof in the presence of an iridium carbonylation catalyst, an alkyl halide co-catalyst, a catalyst promoter selected from ruthenium, osmium and rhenium and optionally a finite concentration of water.

22. A process according to claim 21 wherein the alcohol is methanol, the alkyl halide is methyl iodide, and the carbonylation is conducted with a finite concentration of water.

23. A process according to claim 1 wherein the liquid composition is to be treated is obtained from a distillation column stream.

24. A process according to claim 23 wherein the distillation column stream is selected from the group consisting of a stream from the base of a heavy ends column, a stream from the base of a combined light ends and drying column and a stream from a drying column.

25. A process according to claim 1 wherein the liquid composition is obtained from a gas phase carbonylation process.

26. A process according to claim 1 wherein the corrosion metal is selected from the group consisting of iron, nickel, chromium, manganese, zinc, molybdenum and mixtures thereof.

* * * * *